(12) United States Patent
Lemaire et al.

(10) Patent No.: US 9,339,246 B2
(45) Date of Patent: May 17, 2016

(54) ASSOCIATION OF WIRELESS DETECTOR WITH AN IMAGING APPARATUS

(75) Inventors: Alain Lemaire, Quincy-Voisins (FR); Sylvie Bothorel, Paris (FR); Caroline Jeanneau, Rochemaure (FR)

(73) Assignee: TROPHY, Marne la Vallee (FR)

( * ) Notice: Subject to any disclaimer, the term of this patent is extended or adjusted under 35 U.S.C. 154(b) by 401 days.

(21) Appl. No.: 13/878,072

(22) PCT Filed: Oct. 7, 2010

(86) PCT No.: PCT/IB2010/002952
§ 371 (c)(1),
(2), (4) Date: Apr. 5, 2013

(87) PCT Pub. No.: WO2012/046092
PCT Pub. Date: Apr. 12, 2012

(65) Prior Publication Data
US 2013/0188629 A1    Jul. 25, 2013

(51) Int. Cl.
*A61B 6/14* (2006.01)
*A61B 6/00* (2006.01)
(Continued)

(52) U.S. Cl.
CPC ............... *A61B 6/14* (2013.01); *A61B 5/0013* (2013.01); *A61B 6/4494* (2013.01); *A61B 6/545* (2013.01);
(Continued)

(58) Field of Classification Search
CPC ...... A61B 19/5244; A61B 6/14; A61B 6/145; A61B 6/4494; A61B 2019/5483; A61B 6/032; A61B 6/12; A61B 6/563; A61B 8/565; A61B 5/06; A61B 6/545; A61B 5/0013; A61B 6/548; A61B 6/586; A61B 6/00; A61B 6/54; G06F 19/3418; G06F 19/321; H04W 84/12; H04W 12/04; H04W 4/008; H04W 72/02; H04W 4/043; G06T 2207/10116
USPC ............ 455/435.1, 422.1; 370/338; 709/223, 709/227, 229; 340/539.12, 539.1, 539.11
See application file for complete search history.

(56) References Cited

U.S. PATENT DOCUMENTS 7,463,813 B2    12/2008  Zwart
2005/0054369 A1   3/2005  Murakami
(Continued)

FOREIGN PATENT DOCUMENTS

EP            1 959 588 A1    8/2008

OTHER PUBLICATIONS

International Search Report, dated Jul. 20, 2011, from corresponding PCT application.

*Primary Examiner* — Charles C Jiang
*Assistant Examiner* — Rose Clark
(74) *Attorney, Agent, or Firm* — Young & Thompson

(57) ABSTRACT

A method for directing image data to a dental treatment site wherein a sensor controller is positioned near a programmed radio-frequency identification device at the dental treatment site. A command entry configures the sensor controller to encode and transmit image data content for delivery to a receiving address, according to information obtained from the radio-frequency identification device. A digital sensor that is associated with the sensor controller is positioned in proximity to a subject. Image data is acquired from the digital sensor and transmitted from the sensor controller to a wireless access point, and from the wireless access point to a host computer at the receiving address. The acquired transmitted image data is stored in a computer-accessible electronic memory.

16 Claims, 8 Drawing Sheets

(51) Int. Cl.
*H04W 4/00* (2009.01)
*A61B 5/00* (2006.01)
*H04W 4/04* (2009.01)
*H04W 84/12* (2009.01)

(52) U.S. Cl.
CPC ............... *A61B 6/548* (2013.01); *A61B 6/563* (2013.01); *A61B 6/586* (2013.01); *H04W 4/008* (2013.01); *H04W 4/043* (2013.01); *H04W 84/12* (2013.01)

(56) References Cited

U.S. PATENT DOCUMENTS

| | | | |
|---|---|---|---|
| 2006/0066453 A1* | 3/2006 | Homanfar et al. | 340/686.2 |
| 2006/0094936 A1* | 5/2006 | Russ | 600/300 |
| 2007/0045424 A1* | 3/2007 | Wang | 235/462.46 |
| 2007/0103303 A1* | 5/2007 | Shoarinejad | 340/572.1 |
| 2007/0146130 A1* | 6/2007 | Hannemann et al. | 340/539.22 |
| 2009/0022276 A1 | 1/2009 | Ohara | |
| 2010/0104065 A1 | 4/2010 | Eguchi | |
| 2010/0169423 A1 | 7/2010 | Eguchi | |

* cited by examiner

ASSOCIATION OF WIRELESS DETECTOR WITH AN IMAGING APPARATUS

FIELD OF THE INVENTION

This invention relates generally to digital imaging applications, and in particular to methods and apparatus for associating a digital detector with an imaging apparatus.

BACKGROUND OF THE INVENTION

Wireless image transfer offers a number of benefits in diagnostic imaging applications. The capability to position a digital image detector at an appropriate position relative to the subject that is to be imaged and to obtain an image without the complication of routing a connecting cable between the image detector and a computer or other host processor, has a number of advantages. For example, this capability helps to simplify operator procedures and workflow and to reduce patient discomfort. The wireless transfer feature provides advantages for various types of radiography imaging, in which an image is formed according to exposure energy directed through a tooth or other structure, as well as for image capture using visible or near-visible light.

Dental imaging is one area where wireless image transfer has particular value. The technologist or other practitioner who is performing the image capture function can work more quickly and encounters fewer constraints when positioning an intra-oral camera or radiography detector that is wireless.

As acceptance and use of wireless digital image detectors grows, a number of new problems have been encountered. A small dental practice, for example, may have only one wireless radiography detector or intra-oral camera using wireless image transmission. In such an environment, there is little chance for confusion about which device transmits and which receives the image data. In contrast, a larger practice may use multiple wireless digital image detectors, such as one assigned to each dental treatment chair or grouping of chairs. With two or more detectors at a single location, the likelihood of confusion increases dramatically. Where there are two detectors, for example, each must be assigned to a specific receiving system or problems could result. Sharing the same detector or intra-oral camera between multiple treatment chairs is risky and care must be taken to properly coordinate how these devices and their data are deployed. In an extreme case, image data for a patient could be sent to the wrong receiving system, leading to incorrect diagnosis or even improper treatment.

Conventional wireless data transfer typically uses a wireless networking technology based on the Institute of Electrical and Electronics Engineers (IEEE) 802.11 standard, generally termed WiFi, or some other wireless local area network (LAN) standard. With such a system, radio frequency (RF) signals are encoded with the data to be transmitted. Because these signals are at low power levels, IEEE 802.11 and similar networks operate reliably over only a limited distance, so that the transmitter and a receiving access apparatus are usually no further than about 10 m apart. Thus, for a larger practice or clinic, further complexity and confusion in transmission of wireless images is possible, since multiple wireless routers may be needed in order to serve all of the treatment rooms.

SUMMARY OF THE INVENTION

It is an object of the present invention to provide wireless image data communication in an environment that uses multiple wireless access points. A further object of the present invention is to provide a method for configuring the wireless image data acquisition device for use in any treatment site within an environment with multiple access points.

It is a feature of the present invention that it uses an RFID tag that is programmed with identifying information for a specific treatment or imaging site in an environment with multiple sites and potentially using more than one wireless access point.

An advantage of the apparatus and methods of the present invention relates to the capability to readily share wireless imaging devices between multiple treatment sites, such as between multiple treatment rooms in a larger dental practice, for example.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a method for directing image data to a dental treatment site, the method executed at least in part on a computer system and comprising: positioning a sensor controller near a programmed radio-frequency identification device at the dental treatment site; entering a command that configures the sensor controller to encode and transmit image data content for delivery to a receiving address, according to information obtained from the radio-frequency identification device; positioning a digital sensor that is associated with the sensor controller in proximity to a subject; acquiring image data from the digital sensor and transmitting the acquired image data from the sensor controller to a wireless access point; transmitting the data from the wireless access point to a host computer at the receiving address; and storing the acquired transmitted image data in a computer-accessible electronic memory.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
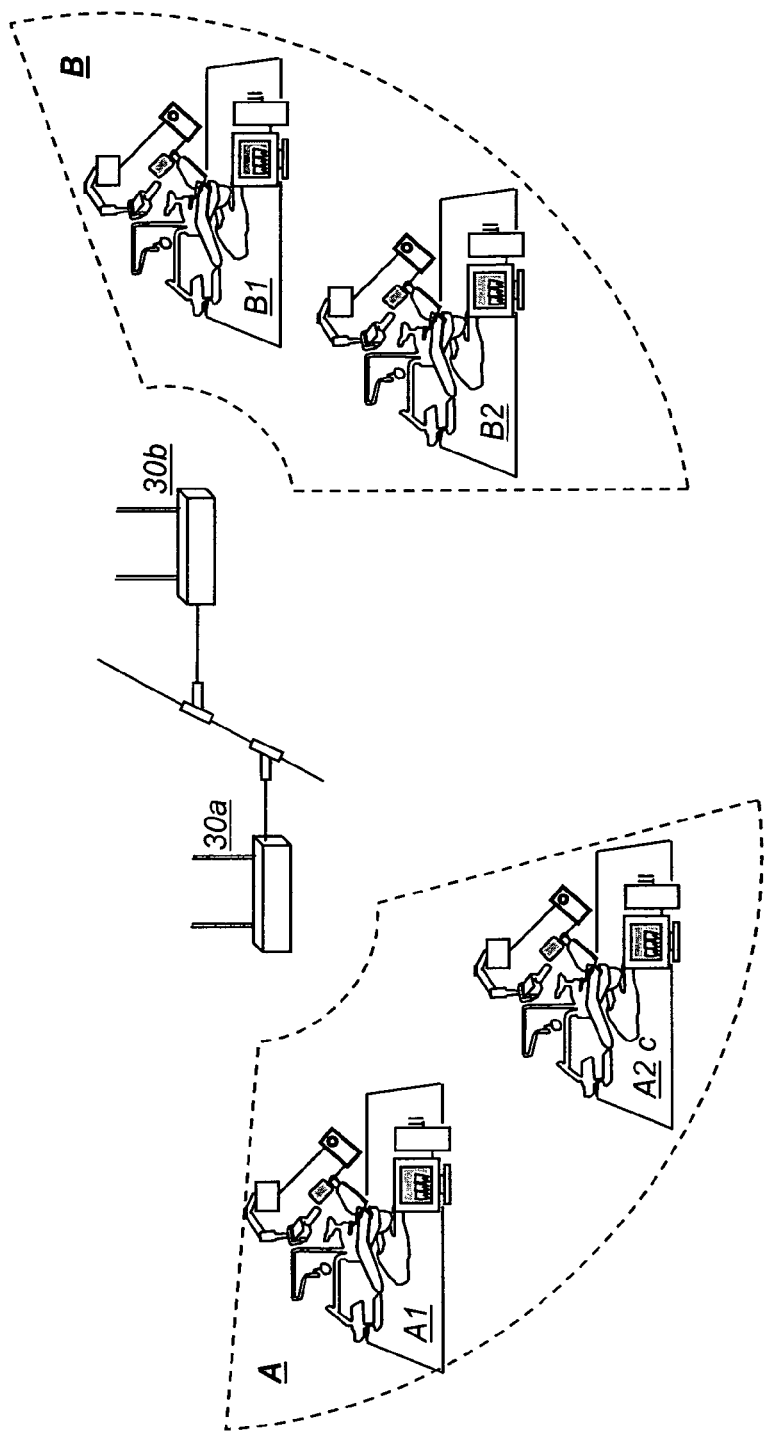
FIG. 1 is a block diagram showing a wireless network arrangement with multiple wireless access points.

The following is a detailed description of the preferred embodiments of the invention, reference being made to the drawings in which the same reference numerals identify the same elements of structure in each of the several figures.

The description of embodiments of the present invention that follows is primarily directed to applications using dental diagnostic images. However, it should be noted that the apparatus and methods of the present invention can be more broadly applied to other applications in which multiple diagnostic images are obtained at different sites that are within the same location.

The block diagram of FIG. 1 shows an example network configuration in which multiple wireless access points 30a and 30b serve multiple dental treatment rooms or sites, labeled A1, A2, B1, and B2. In the arrangement shown, access point 30a serves treatment sites A1 and A2 in area A; access point 30b serves treatment sites B1 and B2 in area B. This type of arrangement can be typical of a larger dental practice, for example, in which distances between treatment rooms are significant or where higher data throughput is desired.

It is noted that distance may not be a factor in determining the number or locations of access points 30a and 30b relative to the number of treatment rooms. If only small amounts of data were transferred, for example, a single access point might serve 4 or more treatment sites that originate images in a suitable manner, with acceptable response time for uploading and transferring the image data. However, since captured dental images can represent a sizable amount of data and because prompt image information delivery is most desirable, bandwidth considerations may dictate that only a few treatment rooms or sites be associated with a specific access point.

Figure 2:
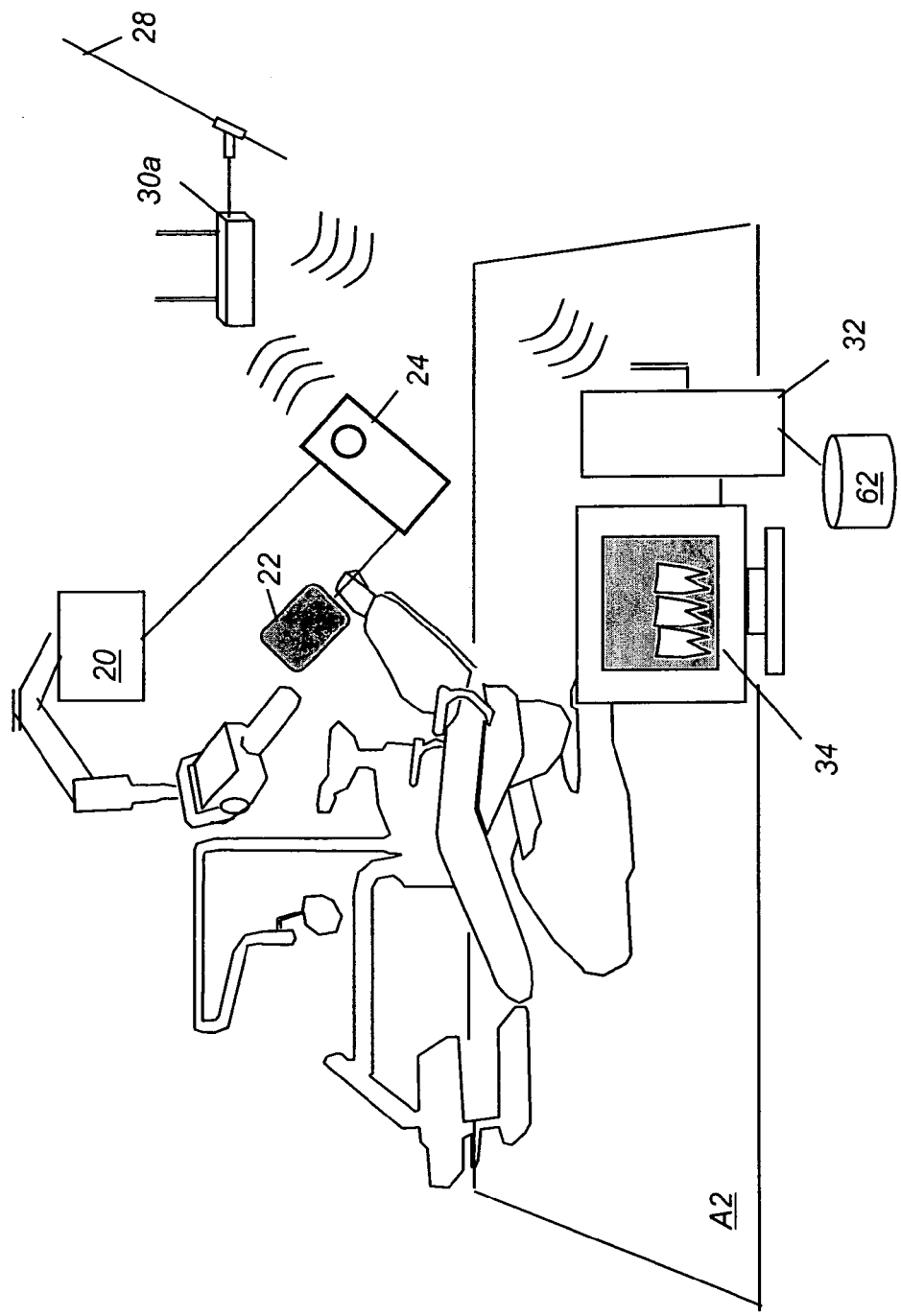
FIG. 2 is a block diagram that shows the use of a wireless digital image detector apparatus where there is a single wireless access point.

The block diagram of FIG. 2 shows the configuration of image acquisition and display apparatus and path of image data for one of the treatment rooms, site A2 of FIG. 1. An x-ray system 20 uses a digital sensor 22 as its detector element for receiving the exposure. This detector element is energizable for generating or acquiring the resulting image data. The acquired image data goes to a controller 24 that then transmits the data wirelessly to access point 30a, connected on a network 28. Access point 30a is also in communication with a host computer 32 that acts as a control monitor for operator command entry and also provides a display 34 in treatment site A2. Connection from access point 30a to host computer 32 is wireless in the example of FIG. 2; alternately, a wired network connection, such as an Ethernet connection, for example, could be used for this data transfer link between the access point 30a and computer 32. A wireless connection is provided between controller 24 and access point 30a.

Host computer 32 stores the received image data in a computer-accessible electronic memory 62 for subsequent display and processing. It should be noted that the term "memory", in the context of the present disclosure, can refer to any type of temporary or longer-lasting data storage workspace used for storing and operating upon image data in a computer system. The memory could be, for example, a long-term storage medium such as magnetic or optical storage. Alternately, the memory could be an electronic circuit, such as random-access memory (RAM) that is used as a temporary buffer or workspace by a microprocessor or other control logic processor device. Display data, for example, is typically stored in a temporary buffer and refreshed as needed in order to provide displayed data. This temporary storage buffer can also be considered to be a memory in this context.

The general arrangement of FIG. 2 is suitable when there is a single detector element, digital sensor 22, and a single controller 24 for a dental office or clinic. However, the use of multiple digital sensors 22 and multiple treatment sites at which images can be acquired complicates the data communication problem, making it necessary to assign the digital sensor 22 to a particular site, such as a treatment room, dental chair, or other specific location.

Figure 3:
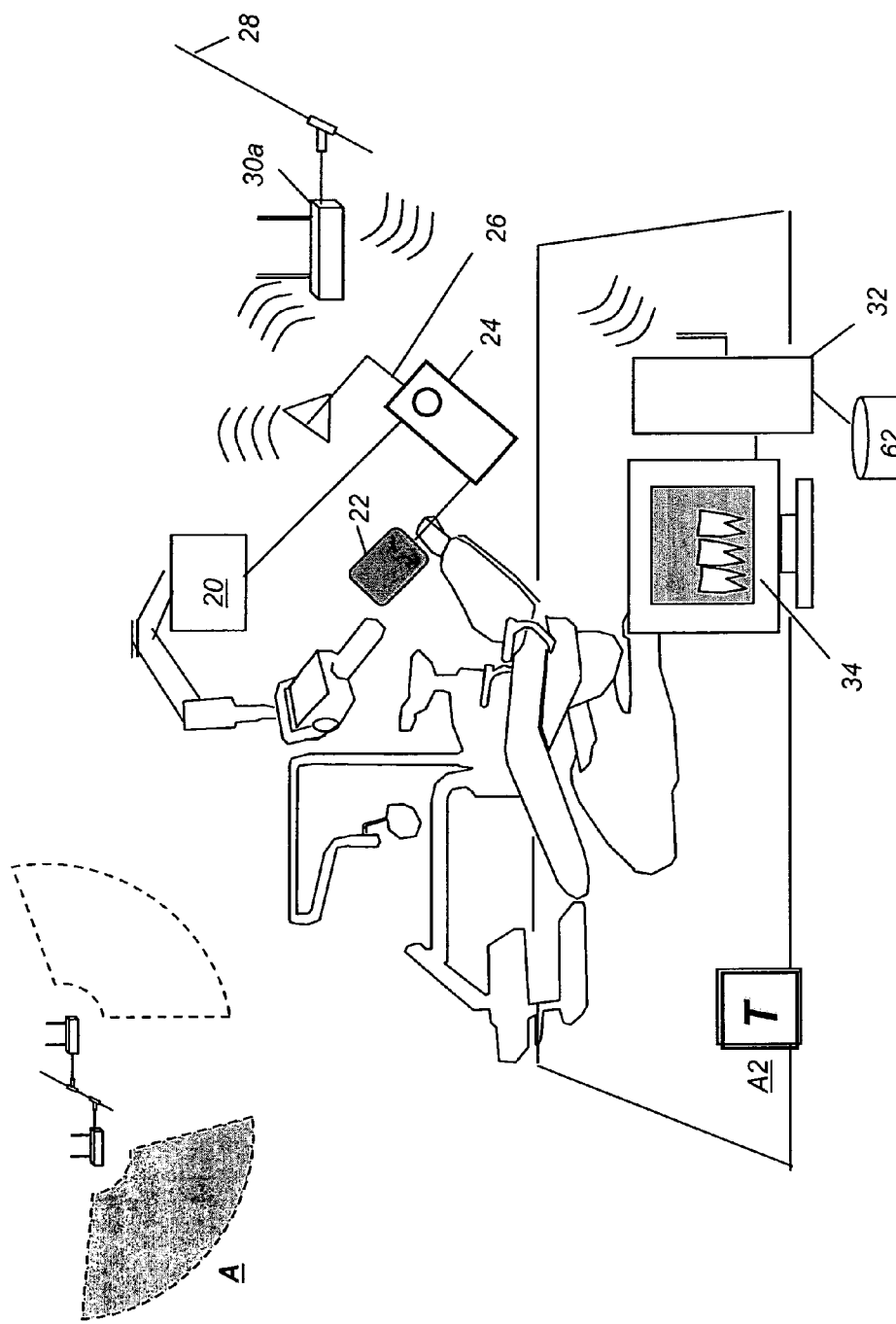
FIG. 3 is a block diagram showing a wireless digital image detector with associated elements in one embodiment of the present invention.

Referring to the block diagram of FIG. 3, there is shown a site configuration according to one embodiment of the present invention. A wireless identifier element such as a Radio-Frequency Identification (RFID) tag T is provided, assigned specifically to treatment site A2, such as attached to the wall of the room, to the treatment chair, or to the host computer 32 at that site, for example. RFID tag T is configured to communicate with a wireless communication device 26 that is provided in or associated with controller 24, as indicated by the antenna schematic symbol in FIG. 3 and subsequent figures. RFID tag T identifies itself so that controller 24 can determine where to send the acquired image data from sensor 22. With this arrangement, the image data sent wirelessly to access point 30a from this location is then automatically directed to host computer 32 at treatment site A2. Using a similar arrangement, any of the treatment sites that are assigned to access point 30a as part of area A have the corresponding assignment to a specific host computer that is installed at or near the treatment site. Additionally, images could also be transferred on the network to a host processor that serves the treatment site, including a host processor that is at a remote location and provides services such as short- or long-term image storage, for example.

RFID devices, such as RFID tags and RFID transponders, are well-known to those skilled in various device identification and tracking arts and are available in a number of types from a range of manufacturers. In the context of the present disclosure, an RFID device or RFID "tag" is a programmable device that, upon excitation by the proper RFID signal, emits encoded data previously stored thereon. An RFID transponder is a device that provides two-way communication, writing identifying data to nearby RFID tags or other devices and interrogating these devices and reading stored data received from other sources. In the system of the present invention, an RFID transponder in controller 24 transmits the obtained image data from sensor 22 to the corresponding access point 30a or 30b.

Figure 4:
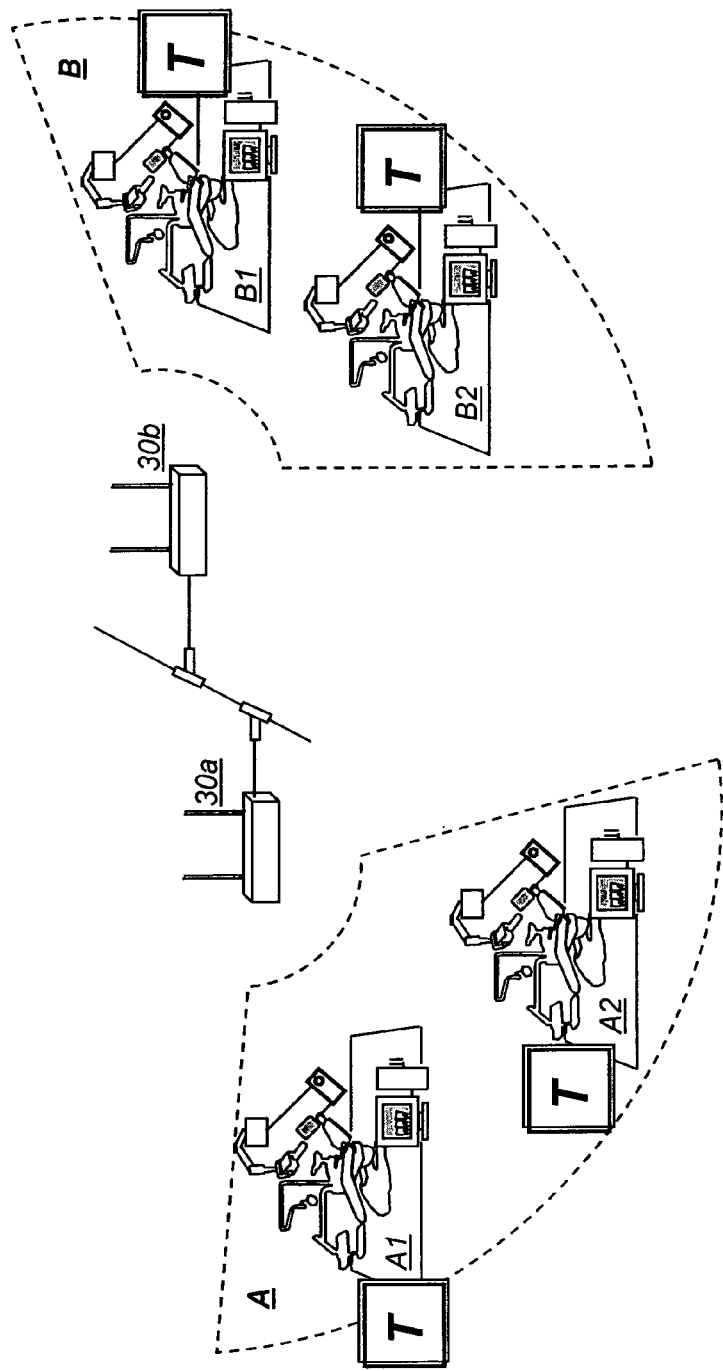
FIG. 4 is a block diagram showing a wireless network arrangement with multiple wireless access points configured according to an embodiment of the present invention.

The block diagram of FIG. 4 shows a network arrangement used at a dental clinic in which two access points 30a and 30 each handle data transfer from two treatment sites, A1 and A2 for area A and B1 and B2 for area B. With such an arrangement, data acquisition at any site can be unambiguously handled and transferred to the appropriate host computer.

Initial Site Setup

Each access point has a unique Service Set Identifier (SSID) that is known to the host computers that use that access point. In order to encode the image data with the proper SSID for delivery to the correct site, the RFID tag T must be programmed to provide the SSID to the sensor 22 and controller 24 used at that site.

Figure 5:
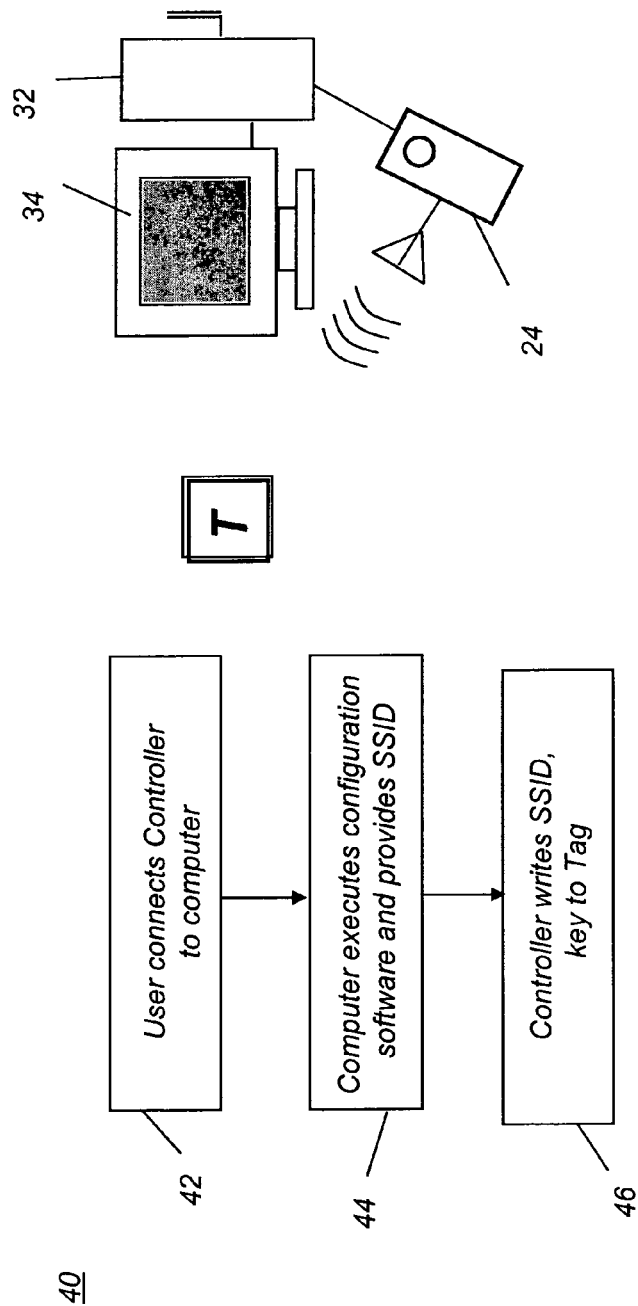
FIG. 5 is a procedural flow diagram that shows RFID tag configuration for a site.

An initial setup procedure is required in order to provide the SSID information that correlates the RFID tag T at any site to its corresponding access point. The workflow diagram of FIG. 5 shows basic steps used as part of an initial setup procedure 40. Setup begins with a connection step 42 in which the user links or connects controller 24 to the host computer 32 at the site. Then, in an execution step 44, a software application running on host computer 32 acknowledges the controller connection and reports the SSID and any needed security key information to controller 24. In a write step 46, controller 24 then broadcasts the SSID, security key, and any other useful information for linking with the access point to RFID tag T. This programs RFID tag T with identifier information.

Once the RFID tag T at a site is programmed, it can communicate with any nearby controller to provide assignment information so that the correct data is directed to host computer 32 at that site.

The software application that is accessed at the site can be installed or downloaded to host computer 32 and configured to obtain the needed information for communication with that computer. The configuration can be automated or may require system administrator or user interaction for setup. In an alternate embodiment, described subsequently, RFID tag T is associated with controller 24 and wireless communication to this identifier element is provided from host computer 32.

Configuration for Daily Use

Figure 6:
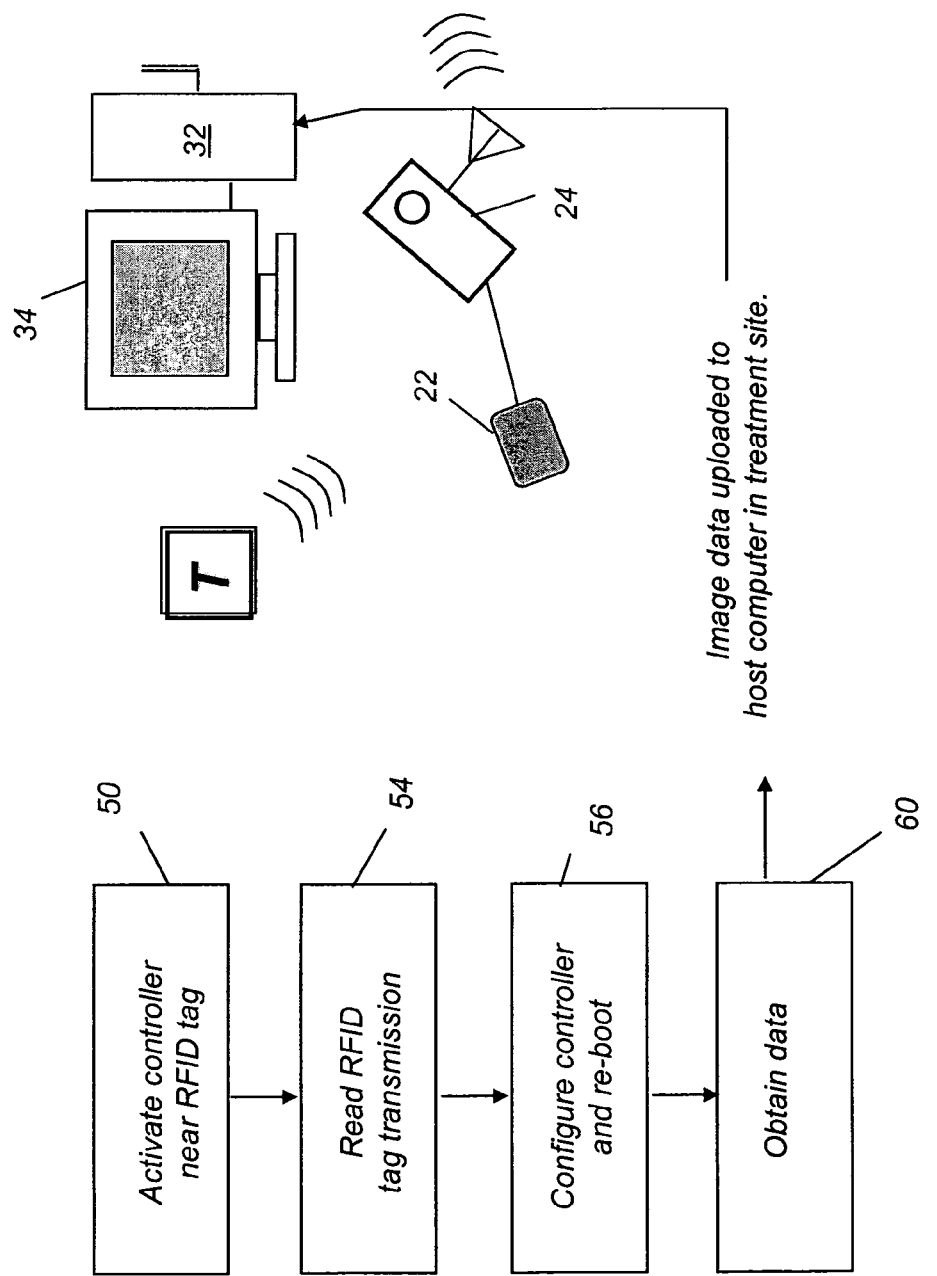
FIG. 6 is a procedural flow diagram for daily operation of a wireless imaging detector system.

The block diagram of FIG. 6 shows the procedural steps that can be used to set up the controller 24 and its digital sensor for use at a specific treatment site. These steps are used when the digital sensor 22 is first assigned to a treatment site or when sensor 22 is moved from one treatment site to another.

In an activation step 50, the operator initiates controller 24 configuration by pressing a control button or by some other action that sends a command prompting a response from the nearby RFID tag T at the site. In one embodiment, for example, the action of moving controller 24 to within a predetermined proximity of RFID tag T enters the command for configuration. In such an embodiment, for example, a periodic polling signal emitted by wireless communication circuitry on controller 24 automatically initiates configuration activity. RFID tag T responds to this configuration command by providing its preprogrammed WiFi configuration information, such as the assigned SSID and any stored security keys that relate to the site, for example. Controller 24 reads this information in a tag 1D receipt step 54. Upon receipt of this information, controller 24 reboots, or is rebooted or otherwise suitably re-configured in a configuration step 56. From this point until its next subsequent re-configuration, controller 24 now encodes the image data that it uploads using the obtained SSID in each obtain data step 60, thereby directing the image data to the appropriate treatment site.

Figure 7:
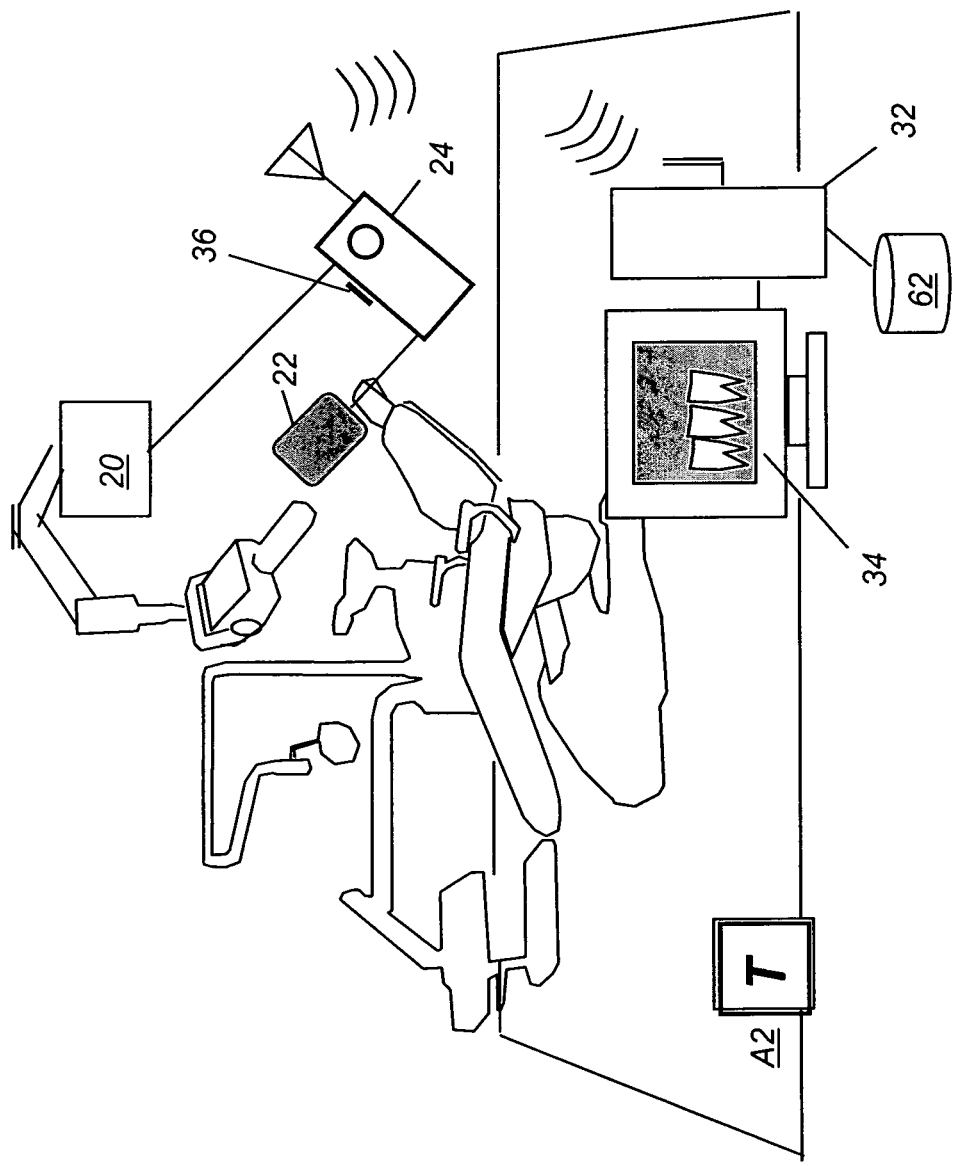
FIG. 7 is a block diagram showing a wireless digital image detector with associated elements for transmitting data wirelessly to a host computer at the treatment site in an alternate embodiment of the present invention.
Figure 8:
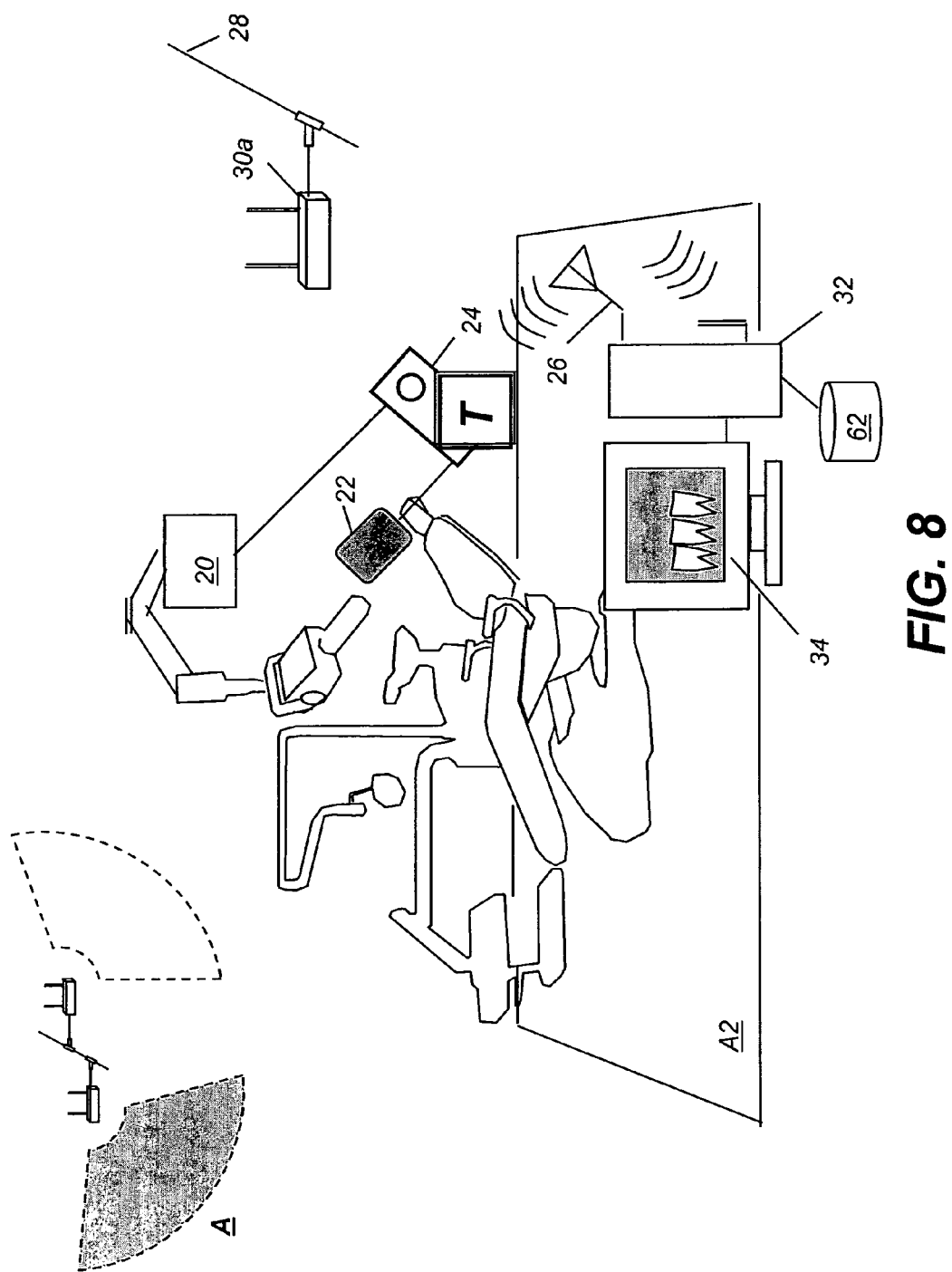
FIG. 8 is a block diagram showing a wireless digital image detector with associated elements for transmitting data to a host computer at the treatment site in another alternate embodiment of the present invention.

In an alternate embodiment, as shown in FIG. 7, the obtained image data from digital sensor 22 is wirelessly transmitted directly to host computer 32 at the treatment site A2. This arrangement may be useful, for example, where problems in wireless communication or with the network require that the access point be bypassed. Alternately, controller 24 can be instructed by commands stored in RFID tag T or entered by the technician to provide image data directly to the site. This alternate mode of operation may be selectable using a selector switch 36 provided on controller 24 or sensor 22, for example. Operating the switch generates a command to redirect image data. FIG. 8 shows an alternate embodiment in which RFID tag T is associated with controller 24 and wireless communication device 26 is linked to host computer 32. With this alternate arrangement, host computer 32 may have multiple wireless links, as shown. This alternate embodiment may be advantageous, for example, where it is desirable to send information from controller 24 and detector 22 both locally to host computer 32 for immediate use and to a remotely connected server for archival.

Embodiments of the present invention allow a flexible network arrangement, so that additional treatment sites, host computers, and other equipment can be readily added to the system without undue complexity. Access point assignments can be modified with minimal setup time or risk of lost data. Image data can also be uploaded to a central host or server that provides storage or archival, allowing the dental practitioner to access a library of stored images obtained from a patient, for example.

Embodiments of the present invention can be used to advantage for obtaining x-ray images for a patient, wherein the images can be displayed only moments after the exposure has been terminated. In addition to x-ray image sensing, embodiments of the present invention may also serve other imaging applications, such as use of an intra-oral camera with a wireless interface, for example. An intra-oral camera can collect still or video images, using white light or other modality images, such as images from fluorescence or optical coherence tomography for example. In addition, a conventional digital camera may be used with this system, such as to obtain intra-oral images or images of external facial features. A sensor for dental ultrasound apparatus could also be used.

Embodiments of the present invention employ software in the form of stored, preprogrammed instructions that are executed by a computer or other type of control logic processor. Stored instructions can be executed at any suitable host processor that is associated with the networked arrangement, such as on host computer 32 or on a processor that is associated with a digital camera, for example.

The invention has been described in detail with particular reference to certain preferred embodiments thereof, but it will be understood that variations and modifications can be effected within the scope of the invention. For example, instructions for uploading SSID and other information from the stored data in RFID tag T may be initiated using a user interface utility, such as a mouse-based selection, typed command entry, or touch screen contact.

Thus, there is provided a method and apparatus for directing image data from a wireless image acquisition apparatus to a dental treatment site.

The invention claimed is:

1. A method for directing image data to a dental treatment site, comprising:

positioning a sensor controller near a programmed radio-frequency identification device located at the dental treatment site;

writing, into the radio-frequency identification device, information concerning an assignment of a wireless access point to the dental treatment site, the assignment being modifiable;

providing a command that configures the sensor controller to encode and transmit image data content for delivery to a receiving address according to information obtained from the radio-frequency identification device, the obtained information associated with the dental treatment site and with the assigned wireless access point;

positioning a digital sensor that is associated with the sensor controller in proximity to a subject;

acquiring image data from the digital sensor and wirelessly transmitting the acquired image data from the sensor controller to the wireless access point;

transmitting the data from the wireless access point to a host computer at the receiving address; and storing the acquired transmitted image data in a computer-accessible electronic memory.

2. The method of claim 1, wherein the digital sensor is an x-ray sensor.

3. The method of claim 1, wherein the digital sensor is taken from the group consisting of an intra-oral camera, a digital camera, a video camera, and a sensor for an ultrasound imaging apparatus.

4. The method of claim 1, wherein providing the command to configure comprises pressing a control button on the controller.

5. The method of claim 1, wherein providing the command to configure the sensor controller comprises entering an instruction on a control monitor.

6. The method of claim 1, wherein providing the command to configure the sensor controller comprises moving the sensor controller to within a predetermined proximity to the programmed radio-frequency identification device.

7. The method of claim 1, further comprising:
displaying the acquired image data.

8. A system for obtaining image data from a treatment site location within a network that has two or more wireless access points, comprising:
a wireless identifier element modifiably encoded with information concerning the treatment site and with an assignment to a wireless access point;
a wireless communication device energizable to interrogate the wireless identifier element and obtain the information concerning the treatment site and the assignment to the wireless access point;
a controller associated with the wireless communication device and in communication with a detector element, the controller configured to obtain digital image data from the detector element, and to wirelessly transmit the obtained digital image data to the assigned wireless access point; and
a host computer, comprising a processor, associated with the treatment site and in communication with the assigned wireless access point, that receives the transmitted digital image and stores the received digital image data in a memory of the host computer.

9. The system of claim 8, further comprising:
a display for displaying the received digital image data.

10. The system of claim 8, wherein the wireless identifier element is a radio-frequency identification tag.

11. The system of claim 8, wherein the wireless communication device is part of the controller.

12. The system of claim 8, wherein the detector element is taken from the group consisting of a digital x-ray detector, and intra-oral camera, a digital camera, a video camera, and a sensor for an ultrasound imaging apparatus.

13. A system for obtaining image data from a site location within a network that has at least first and second sites and at least first and second wireless access points, comprising:
a wireless identifier element located at each of the at least first and second sites, wherein the wireless identifier element is modifiably encoded with information concerning the site location and an assignment of the site location to one of the first or second wireless access point;
a wireless communication device, associated with a controller at each of the first and second sites, the wireless communication device being energizable to interrogate the wireless identifier element and obtain at least the information concerning the site location and the assignment to the one of the first or second wireless access point,
the controller, at each of the first and second sites, and in communication with a detector element at the site location, the controller configured to obtain digital image data from the detector element, and to direct the digital image data to the assigned wireless access point; and
a host computer, comprising a processor, associated with the at least first and second sites and in communication with the assigned wireless access point, that receives the corresponding site for receiving digital image data and that stores the received digital image data in a memory of the host computer.

14. The system of claim 13, further comprising:
a display for displaying the received image data.

15. The system of claim 13, wherein the wireless identifier element is an RFID tag.

16. A system for obtaining image data at a dental treatment site, comprising:
a detector element that is energizable for acquiring the image data and in communication with a controller;
a wireless identifier element, located at the dental treatment site and associated with the controller;
a host computer, comprising a processor, associated with the dental treatment site and comprising a wireless communication device, the wireless communication device being energizable to interrogate the wireless identifier element and obtain from the wireless identifier element at least information concerning the controller; and
a wireless access point, in wireless communication with any of the host computer and the controller,
wherein the wireless communication device obtains, from the wireless identifier element, information concerning an assignment to the wireless access point, and
wherein the wireless access point receives the acquired image data transmitted from the dental treatment site based on the information concerning the controller obtained by the wireless communication device, the controller configured to transmit the image data from the detector element to the wireless access point based on the information concerning the assignment to the wireless access point.

* * * * *